United States Patent
Kakitsuba et al.

(10) Patent No.: US 12,178,693 B2
(45) Date of Patent: Dec. 31, 2024

(54) ABSORBENT ARTICLE

(71) Applicant: LIVEDO CORPORATION, Ehime (JP)

(72) Inventors: Yusuke Kakitsuba, Tokushima (JP); Yoshihisa Ota, Osaka (JP)

(73) Assignee: LIVEDO CORPORATION, Ehime (JP)

( * ) Notice: Subject to any disclaimer, the term of this patent is extended or adjusted under 35 U.S.C. 154(b) by 550 days.

(21) Appl. No.: 17/603,402

(22) PCT Filed: Mar. 11, 2020

(86) PCT No.: PCT/JP2020/010421
§ 371 (c)(1),
(2) Date: Oct. 13, 2021

(87) PCT Pub. No.: WO2020/213303
PCT Pub. Date: Oct. 22, 2020

(65) Prior Publication Data
US 2022/0211554 A1    Jul. 7, 2022

(30) Foreign Application Priority Data
Apr. 15, 2019  (JP) ................. 2019-077285

(51) Int. Cl.
*A61F 13/84* (2006.01)
*A61F 13/511* (2006.01)

(52) U.S. Cl.
CPC .... *A61F 13/8405* (2013.01); *A61F 13/51113* (2013.01); *A61F 2013/8408* (2013.01); *A61F 2013/845* (2013.01)

(58) Field of Classification Search
CPC ............ A61F 13/51113; A61F 13/8405; A61F 2013/51059; A61F 2013/51076;
(Continued)

(56) References Cited

U.S. PATENT DOCUMENTS 9,018,435 B2 *  4/2015  Kawashima ............ A61L 15/56
                                                    604/361
9,801,830 B2 * 10/2017  Darcy .................... A61K 47/36
(Continued)

FOREIGN PATENT DOCUMENTS

CN   101518658    9/2009
CN   106770803    5/2017
(Continued)

OTHER PUBLICATIONS

JP_2016187549_A Translation (Year: 2016).*
(Continued)

*Primary Examiner* — Catharine L Anderson
(74) *Attorney, Agent, or Firm* — Wenderoth, Lind & Ponack, L.L.P.

(57) ABSTRACT

[Problem] To provide an absorbent article further suppressing occurrence of malodor after absorbing body fluid.
[Solution] An absorbent article comprising a liquid permeable top sheet disposed on a skin surface side, a liquid impermeable back sheet disposed on an external surface side, and an absorbent body disposed between the top sheet and the back sheet, wherein the absorbent body has a water absorbent layer including a water absorbent resin powder, fumaric acid is disposed at a position being able to be in contact with body fluid absorbed in the absorbent article, and a polyphenol compound is disposed closer to the skin surface side than the back sheet.

19 Claims, 2 Drawing Sheets

(58) Field of Classification Search
CPC ...... A61F 2013/5109; A61F 2013/8408; A61F 2013/8435; A61F 2013/845
See application file for complete search history.

(56) References Cited

U.S. PATENT DOCUMENTS

| | | | | |
|---|---|---|---|---|
| 10,195,091 | B2* | 2/2019 | Rosati | ...................... D04H 1/42 |
| 2008/0300558 | A1* | 12/2008 | Brusk | ............... A61F 13/47227 |
| | | | | 604/385.03 |
| 2010/0158840 | A1 | 6/2010 | Hiramoto et al. | |
| 2016/0051423 | A1 | 2/2016 | Ota et al. | |

FOREIGN PATENT DOCUMENTS

| | | |
|---|---|---|
| JP | 2009-530014 | 8/2009 |
| JP | 3169106 | 7/2011 |
| JP | 2014-204799 | 10/2014 |
| JP | 2016-10593 | 1/2016 |
| JP | 2016-138349 | 8/2016 |
| JP | 2016-187549 | 11/2016 |
| JP | 2017-184962 | 10/2017 |
| JP | 2018-68911 | 5/2018 |
| JP | 2018-71022 | 5/2018 |
| JP | 2019-43103 | 3/2019 |

OTHER PUBLICATIONS

Office Action issued Jul. 25, 2023 in corresponding Japanese Patent Application No. 2019-077285, with English machine translation.
Extended European Search Report issued Nov. 21, 2022 in correpsonding European Patent Application No. 20790896.3.
International Search Report (ISR) issued Jun. 16, 2020 in International (PCT) Application No. PCT/JP2020/010421.

* cited by examiner

ABSORBENT ARTICLE

FIELD OF THE INVENTION

The present invention relates to an absorbent article including a water absorbent resin powder, and particularly relates to deodorization of an absorbent article after absorbing body fluid.

DESCRIPTION OF THE RELATED ART

An absorbent article such as a diaper, a sanitary napkin, and a pad for incontinent persons is used to absorb and retain body fluid excreted from body such as urine and menstrual blood. A measure against unpleasant odor from the absorbent article being used or discarded after use is desired. An absorbent article reducing such the unpleasant odor has been proposed.

For example, patent literature 1 discloses an absorbent article comprising an absorbent body, and a fumaric acid-supporting sheet disposed on a skin surface side of the absorbent body, wherein the fumaric acid-supporting sheet is a sheet supporting fumaric acid particles having an average particle size of 30 μm or less, and/or a sheet having at least a part of constituent fibers coated with fumaric acid (refer to claim 1 and paragraph 0013 of patent literature 1).

In addition, patent literature 2 discloses an absorbent article comprising an absorbent body, a top sheet disposed on a skin side of the absorbent body, and a back sheet disposed on an external side of the absorbent body, wherein the back sheet has a nonwoven fabric formed from a semisynthetic cellulose fiber and laminated on an external side of a moisture permeable film. The patent literature 2 discloses the nonwoven fabric includes a deodorizer, and exemplifies condensed tannin as the deodorizer (refer to claims 1, 3 and paragraph 0037 of patent literature 2).

CITATION LIST

Patent Literature

Patent literature 1: JP 2014-204799 A
Patent literature 2: JP 2018-68911 A

SUMMARY OF THE INVENTION

Problem to be Solved by the Invention

Although occurrence of malodor in the conventional absorbent article after absorbing body fluid is lowered, there is still room for improvement. An objective of the present invention is to provide an absorbent article further inhibiting occurrence of malodor after absorbing body fluid.

Solution to Solve Problem

The absorbent article according to the present invention comprises a liquid permeable top sheet disposed on a skin surface side, a liquid impermeable back sheet disposed on an external surface side, and an absorbent body disposed between the top sheet and the back sheet, wherein the absorbent body has a water absorbent layer including a water absorbent resin powder, fumaric acid is disposed at a position being able to be in contact with the body fluid absorbed in the absorbent article, and a polyphenol compound is disposed closer to the skin surface side than the back sheet.

Disposing fumaric acid at the portion being able to be in contact with the body fluid or the like absorbed in the absorbent article can prevent occurrence of malodor from the absorbent article after absorbing the body fluid or the like. Further, disposing the polyphenol compound can capture the odor component occurring from the absorbed body fluid. Thus, the absorbent article according to the present invention can inhibit occurrence of malodor after absorbing the body fluid.

Effect of the Invention

According to the present invention, an absorbent article further inhibiting occurrence of malodor after absorbing body fluid is obtained.

DESCRIPTION OF THE PREFERRED EMBODIMENT

Figure 1:
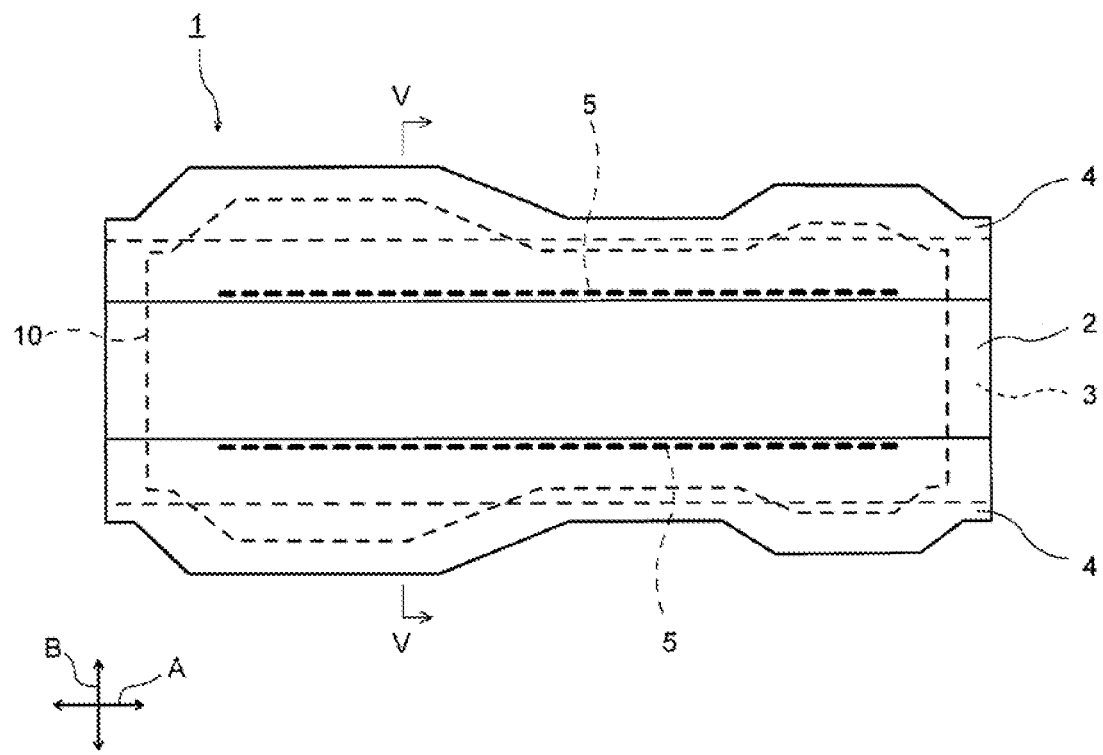
FIG. 1 is a planar view of an example of the absorbent article according to the present invention.

The absorbent article according to the present invention comprises a liquid permeable top sheet disposed on a skin surface side, a liquid impermeable back sheet disposed on an external surface side, and an absorbent body disposed between the top sheet and the back sheet, and the absorbent body has a water absorbent layer including a water absorbent resin powder. Furthermore, the absorbent article according to the present invention has fumaric acid disposed at a position being able to be in contact with the body fluid absorbed in the absorbent article, and a polyphenol compound disposed closer to the skin surface side than the back sheet.

Fumaric acid has an action of inhibiting proliferation of putrefactive bacteria. Thus, disposing fumaric acid at the portion (e.g. the top sheet, or the portion around the water absorbent resin powder) being able to be in contact with the body fluid or the like absorbed in the absorbent article can inhibit proliferation of putrefactive bacteria, and hence can prevent occurrence of malodor from the absorbent article after absorbing the body fluid or the like. In addition, the polyphenol compound can capture the odor component. Thus, disposing the polyphenol compound closer to the skin surface side than the back sheet can capture the odor component occurring from the absorbed body fluid. The odor component occurring from the absorbed body fluid is reduced by fumaric acid and captured by the polyphenol compound in the absorbent article according to the present invention, thus leakage of the odor out of the absorbent article is inhibited. Thus, the absorbent article according to the present invention can inhibit occurrence of malodor after absorbing body fluid.

The absorbent article according to the present invention comprises a liquid permeable top sheet disposed on a skin surface side and a liquid impermeable back sheet disposed on an external surface side.

(Top Sheet)

The top sheet is disposed on a closest side of the absorbent article to the wearer to rapidly capture the body fluid from the wearer and move the body fluid toward the water absorbent resin powder. As the top sheet, a liquid permeable sheet material, for example, a nonwoven fabric formed of a hydrophilic fiber can be used. The nonwoven fabric used as the top sheet is, for example, a point-bonded nonwoven fabric, air-through nonwoven fabric, spunlace nonwoven fabric, or spunbond nonwoven fabric. As the hydrophilic fiber for forming these nonwoven fabrics, cellulose, rayon, cotton, and the like are usually used. It is noted that as the top sheet, a liquid permeable nonwoven fabric formed of a hydrophobic fiber (for example, polypropylene, polyethylene, polyester, and polyamide) whose surface is hydrophilized with a surfactant may be used.

(Back Sheet)

The back sheet is disposed on an outermost side of the absorbent article to prevent the body fluid or the like from leaking out. As the liquid impermeable sheet used as the back sheet, a water-repellent or liquid impermeable nonwoven fabric (for example, a spunbond nonwoven fabric, meltblown nonwoven fabric, and SMS (spunbond-meltblown-spunbond) nonwoven fabric) formed of a hydrophobic fiber (for example, polypropylene, polyethylene, polyester, and polyamide), or a water-repellent or liquid impermeable plastic film is used to prevent the body fluid reaching the liquid impermeable sheet from oozing out of the absorbent article. When the plastic film is used as the liquid impermeable sheet, a moisture permeable (air permeable) plastic film is preferably used from the standpoint of preventing the humid feeling and enhancing the wearer's comfortableness.

(Absorbent Body)

The absorbent article comprises an absorbent body disposed between the top sheet and the back sheet. The absorbent body has at least one water absorbent layers, and the water absorbent layers include a water absorbent resin powder. It is noted that the absorbent body comprised in the absorbent article may be one or at least two.

(Water Absorbent Resin Powder)

The water absorbent resin powder will be explained. The water absorbent resin particles absorb and retain the body fluid excreted from the user. It is noted that examples of the body fluid include urine, blood, sweat, exudate, watery stool, and soft stool. The water absorbent resin powder used in the present invention is preferably, but not particularly limited to, a crosslinked polymer having acrylic acid as a constituent component and having carboxyl groups being at least partially neutralized. The amount of the acrylic acid component constituting the crosslinked polymer is preferably 50 mass % or more, more preferably 90 mass % or more, and even more preferably 95 mass % or more, and is preferably 99 mass % or less, more preferably 97 mass % or less. If the amount of the acrylic acid component falls within the above range, the obtained water absorbent resin powder easily expresses the desired absorption performance.

Examples of the cation for neutralizing at least a part of the carboxyl groups of the crosslinked polymer include, but is not particularly limited to, an alkali metal ion such as lithium, sodium and potassium; and an alkaline earth metal ion such as magnesium and calcium. Among them, at least a part of the carboxyl groups of the crosslinked polymer is preferably neutralized with a sodium ion. It is noted that the neutralization of the carboxyl groups of the crosslinked polymer can be conducted by neutralizing the carboxyl groups of the crosslinked polymer obtained by polymerization, or alternatively be conducted by using a monomer which has been neutralized in advance to form the crosslinked polymer.

The neutralization degree of the carboxyl groups of the crosslinked polymer is preferably 55 mole % or more, more preferably 60 mole % or more. If the neutralization degree is excessively low, the obtained water absorbent resin powder may have lowered absorption performance. In addition, the upper limit of the neutralization degree is not particularly limited, and all the carboxylic groups can be neutralized. It is noted that the neutralization degree is calculated according to the following formula.

Neutralization degree (mole %)=100×[Number of moles of neutralized carboxyl groups in crosslinked polymer]/[Total number of moles of carboxyl groups in crosslinked polymer (including neutralized and unneutralized carboxyl groups)]

The crosslinked polymer is preferably obtained by polymerizing an unsaturated monomer composition containing (a1) a water-soluble ethylenically unsaturated monomer and/or (a2) a hydrolyzable monomer, and (b) an internal crosslinking agent.

As (a1) the water-soluble ethylenically unsaturated monomer, a monomer having at least one water-soluble substituent and an ethylenically unsaturated group, or the like can be used. The water-soluble monomer means a monomer having a property of being dissolved at least in an amount of 100 g in 100 g of water at 25° C. In addition, (a2) the hydrolyzable monomer is hydrolyzed with water at 50° C. by the action of a catalyst (an acid, base, or the like) where necessary, to generate (a1) the water-soluble ethylenically unsaturated monomer. The hydrolysis of (a2) the hydrolyzable monomer may be conducted during, after, or both during and after the polymerization of the crosslinked polymer. However, the hydrolysis of (a2) the hydrolyzable monomer is preferably conducted after the polymerization of the crosslinked polymer in light of the molecular weight of the obtained water absorbent resin powder.

Examples of the water-soluble substituent include a carboxy group, a sulfo group, a sulfoxy group, a phosphono group, a hydroxy group, a carbamoyl group, an amino group, salts thereof, and an ammonium salt. A salt of a carboxy group (carboxylate), a salt of a sulfo group (sulfonate), and an ammonium salt are preferable. In addition, examples of the salt include a salt of an alkali metal such as lithium, sodium and potassium, and a salt of an alkaline earth metal such as magnesium and calcium. The ammonium salt may be any of salts of primary to tertiary amines or a quaternary ammonium salt. Among these salts, the alkali metal salt and ammonium salt are preferable, the alkali metal salt is more preferable, and the sodium salt is even more preferable in light of absorption properties.

As the water-soluble ethylenically unsaturated monomer having the carboxy group and/or the salt thereof, an unsaturated carboxylic acid having 3 to 30 carbon atoms and/or a salt thereof is preferable. Specific examples of the water-soluble ethylenically unsaturated monomer having the carboxy group and/or the salt thereof include an unsaturated monocarboxylic acid and/or a salt thereof such as (meth)acrylic acid, (meth)acrylic acid salt, crotonic acid and cinnamic acid; an unsaturated dicarboxylic acid and/or a salt thereof such as maleic acid, maleic acid salt, fumaric acid, citraconic acid and itaconic acid; and a monoalkyl (1 to 8 carbon atoms) ester of an unsaturated dicarboxylic acid and/or a salt thereof such as maleic acid monobutyl ester, fumaric acid monobutyl ester, ethylcarbitol monoester of maleic acid, ethylcarbitol monoester of fumaric acid, citraconic acid monobutyl ester, and itaconic acid glycol monoester. It is noted that "(meth)acrylic" means "acrylic" and/or "methacrylic" in the description of the present invention.

(a2) The hydrolyzable monomer is not particularly limited, and an ethylenically unsaturated monomer having at least one hydrolyzable substituent that becomes a water-soluble substituent by hydrolysis is preferable. Examples of the hydrolyzable substituent include a group including an acid anhydride, a group including an ester bond, and a cyano group.

As the ethylenically unsaturated monomer having the group including the acid anhydride, an unsaturated dicarboxylic acid anhydride having 4 to 20 carbon atoms can be used, and examples thereof include maleic acid anhydride, itaconic acid anhydride, and citraconic acid anhydride. Examples of the ethylenically unsaturated monomer having the group including the ester bond include a lower alkyl ester of a monoethylenically unsaturated carboxylic acid such as methyl (meth)acrylate and ethyl (meth)acrylate; and an ester of a monoethylenically unsaturated alcohol such as vinyl acetate and (meth)allyl acetate. Examples of the ethylenically unsaturated monomer having the cyano group include a nitrile compound having 3 to 6 carbon atoms and including a vinyl group such as (meth)acrylonitrile and 5-hexenenitrile.

As (a1) the water-soluble ethylenically unsaturated monomer and (a2) the hydrolyzable monomer, those disclosed in JP 3648553 B, JP 2003-165883 A, JP 2005-75982 A and JP 2005-95759 A may also be used. Each of (a1) the water-soluble ethylenically unsaturated monomer and (a2) the hydrolyzable monomer may be used solely, or two or more of them may be used in combination.

The unsaturated monomer composition may further contain (a3) other vinyl monomer that is copolymerizable with (a1) the water-soluble ethylenically unsaturated monomer and (a2) the hydrolyzable monomer. Examples of (a3) the copolymerizable other vinyl monomer include, but are not limited to, a hydrophobic vinyl monomer.

As (a3) the other vinyl monomer, those disclosed in JP 3648553 B, JP 2003-165883 A, JP 2005-75982 A and JP 2005-95759 A may also be used.

In the present invention, as (a1) the water-soluble ethylenically unsaturated monomer and/or (a2) the hydrolyzable monomer, (a1) acrylic acid or acrylic acid salt, or (a2) the hydrolyzable monomer generating acrylic acid or acrylic acid salt by hydrolysis is preferably used, from the viewpoint of obtaining a crosslinked polymer mainly composed of acrylic acid. The amount of (a1) acrylic acid or acrylic acid salt, or (a2) the hydrolyzable monomer generating acrylic acid or acrylic acid salt by hydrolysis in the unsaturated monomer composition forming the crosslinked polymer is preferably 50 mass % or more, more preferably 90 mass % or more, and even more preferably 95 mass % or more, and is preferably 99 mass % or less, more preferably 97 mass % or less.

Examples of (b) the internal crosslinking agent include (b1) an internal crosslinking agent having at least two ethylenically unsaturated groups, (b2) an internal crosslinking agent having at least one ethylenically unsaturated group, and at least one functional group reactive with the water-soluble substituent of (a1) the water-soluble ethylenically unsaturated monomer and/or the water-soluble substituent generated by hydrolysis of (a2) the hydrolyzable monomer, and (b3) an internal crosslinking agent having at least two functional groups reactive with the water-soluble substituent of (a1) the water-soluble ethylenically unsaturated monomer and/or the water-soluble substituent generated by hydrolysis of (a2) the hydrolyzable monomer.

As (b) the internal crosslinking agent, (b1) the internal crosslinking agent having at least two ethylenically unsaturated groups is preferable, a poly(meth)allyl ether of a polyol having 2 to 10 carbon atoms is more preferable, triallyl cyanurate, triallyl isocyanurate, tetraallyloxy ethane or pentaerythritol triallyl ether is even more preferable, and pentaerythritol triallyl ether is most preferable, from the viewpoint of the absorption performance (in particular, absorption amount and absorption speed) or the like.

As (b) the internal crosslinking agent, those disclosed in JP 3648553 B, JP 2003-165883 A, JP 2005-75982 A and JP 2005-95759 A may also be used.

As the polymerization method of the crosslinked polymer, a conventional method or the like can be used, and a solution polymerization method, an emulsion polymerization method, a suspension polymerization method, and a reversed-phase suspension polymerization method can be used. In addition, the polymerization liquid at the polymerization may be in a form of a thin film, mist, or the like. As the method for controlling the polymerization, an adiabatic polymerization method, a temperature-controlled polymerization method, an isothermal polymerization method, or the like can be used. As the polymerization method, the solution polymerization method is preferable, and an aqueous solution polymerization method is more preferable since an organic solvent or the like is not used and it is advantageous in terms of production cost.

The crosslinked polymer may be pulverized after being dried. The pulverization method is not particularly limited, and for example, an ordinary pulverizing apparatus such as a hammer type pulverizer, an impact type pulverizer, a roll type pulverizer, and a jet streaming type pulverizer may be used. The particle size of the pulverized crosslinked polymer may be adjusted by sieving where necessary.

The weight average particle size (μm) of the crosslinked polymer which has been sieved where necessary is preferably 300 μm or more, more preferably 350 μm or more, and even more preferably 400 μm or more, and is preferably 500 μm or less, more preferably 480 μm or less, and even more preferably 450 μm or less. If the weight average particle size (μm) falls within the above range, the absorption performance is better.

It is noted that the weight average particle size is measured with a ro-tap test sieve shaker and standard sieves (JIS Z8801-1: 2006) according to the method described in Perry's Chemical Engineers Handbook, Edition $6^{th}$ (The McGraw-Hill Book Companies, 1984, Page 21). In other words, JIS standard sieves having a mesh size of 1000 μm, 850 μm, 710 μm, 500 μm, 425 μm, 355 μm, 250 μm, 150 μm, 125 μm, 75 μm and 45 μm and a tray are combined in this order from the top downward. About 50 g of the test particles are placed on the uppermost sieve, and shook for 5 minutes with the ro-tap test sieve shaker. The masses of the test particles on each sieve and on the tray are weighed, the total mass is taken as 100 mass % to calculate the mass ratio of the particles on each sieve, the value of the mass ratio is plotted on a logarithmic probability paper {horizontal axis: mesh size of sieve (particle size), vertical axis: mass ratio}, and a line is drawn to connect each point. The particle size corresponding to the mass ratio of 50 mass % is obtained and adopted as the weight average particle size.

The crosslinked polymer may be further subjected to surface crosslinking where necessary. As the crosslinking agent (surface crosslinking agent) for conducting the surface crosslinking, the same one as (b) the internal crosslinking agent can be used. As the surface crosslinking agent, (b3) the crosslinking agent having at least two functional groups reactive with the water-soluble substituent of (a1) the water-soluble ethylenically unsaturated monomer and/or the water-soluble substituent generated by hydrolysis of (a2) the hydrolyzable monomer is preferable, the polyvalent glycidyl is more preferable, ethylene glycol diglycidyl ether or glycerin diglycidyl ether is even more preferable, and ethylene glycol diglycidyl ether is most preferable, from the viewpoint of the absorption performance or the like of the water absorbent resin powder.

The crosslinked polymer may be further treated with a surface modifier. Examples of the surface modifier include a polyvalent metal compound such as aluminum sulfate, potassium alum, ammonium alum, sodium alum, (poly) aluminum chloride, and hydrates thereof; a polycation compound such as polyethyleneimine, polyvinylamine, and polyallylamine; inorganic fine particles; a surface modifier including a hydrocarbon group having a fluorine atom; and a surface modifier having a polysiloxane structure.

The method for treating the crosslinked polymer with the surface modifier is not particularly limited, as long as treatment is conducted such that the surface modifier is present on the surface of the crosslinked polymer. However, the surface modifier is preferably mixed with a dried product of the crosslinked polymer from the viewpoint of controlling the amount of the surface modifier on the surface. It is noted that the mixing is preferably uniformly conducted.

The shape of the water absorbent resin powder is not particularly limited, and examples thereof include an indefinite crushed shape, scale shape, pearl shape, and rice grain shape. Among them, the indefinite crushed shape is preferable from the viewpoint that the water absorbent resin powder in the indefinite crushed shape is well entangled with fibrous materials in applications such as diaper and thus there is little possibility for the water absorbent resin powder to fall off from the fibrous materials.

The water absorbent resin powder may further include an additive such as an antiseptic, fungicide, antibacterial agent, antioxidant, ultraviolet absorbent agent, coloring agent, perfuming agent, deodorizer, inorganic powder, and organic fibrous material Examples of the additive include those listed in JP 2003-225565 A and JP 2006-131767 A.

(Water Absorbent Fiber)

The water absorbent layer may further include a water absorbent fiber in addition to the water absorbent resin powder. Examples of the water absorbent fiber include a pulp fiber. The amount of the water absorbent fiber is preferably 25 parts by mass or more, more preferably 50 parts by mass or more, and even more preferably 100 parts by mass or more, and is preferably 700 parts by mass or less, more preferably 600 parts by mass or less, and even more preferably 500 parts by mass or less, with respect to 100 parts by mass of the water absorbent resin powder disposed in the water absorbent layer. It is noted that the water absorbent layer preferably does not include an acetate fiber. It is also preferable that the water absorbent fiber consists of the pulp fiber.

(Fiber Base Material)

The water absorbent layer may include a fiber base material in addition to the water absorbent resin powder. Examples of the fiber base material include a thermal bonding fiber. The thermal bonding fiber is used to enhance shape-retention. Specific examples of the thermal bonding fiber include a polyolefin fiber such as a polyethylene fiber and a polypropylene fiber, a polyester fiber, and a composite fiber. If the water absorbent material of the water absorbent layer consists of the water absorbent resin powder, the water absorbent layer can be made thin. The water absorbent layer including the fiber base material is superior in dispersibility of body fluid.

Examples of the embodiment of the absorbent body include an embodiment having the water absorbent resin powder fixed on a liquid permeable sheet; an embodiment having the water absorbent resin powder wrapped with a liquid permeable sheet; and an embodiment having the water absorbent resin powder held between a liquid permeable first sheet and a liquid permeable second sheet. Examples of the liquid permeable sheet include a point-bonded nonwoven fabric, air-through nonwoven fabric, spunlace nonwoven fabric, spunbond nonwoven fabric, and tissue paper. The absorbent body may have only one water absorbent layer, or have at least two water absorbent layers. It is noted that wrapping the water absorbent layer with the liquid permeable sheet is a state that at least 70% of the surface of the water absorbent layer is wrapped with the liquid permeable sheet.

(Fumaric Acid)

The absorbent article has fumaric acid disposed in a position being able to be in contact with the body fluid absorbed in the absorbent article.

The position where fumaric acid is disposed is not particularly limited, as long as the position can be in contact with the body fluid absorbed in the absorbent article, and examples thereof include the top sheet, absorbent body, back sheet, sheet disposed between the top sheet and the absorbent body, and sheet disposed between the absorbent body and the back sheet. In case of disposing fumaric acid in the absorbent body, fumaric acid can be disposed in the water absorbent layer, or disposed in the liquid permeable sheet constituting the absorbent body. In addition, fumaric acid may be disposed only at one member, or disposed at two or more members.

The amount of fumaric acid is preferably 0.0009 part by mass or more, more preferably 0.0018 part by mass or more, and even more preferably 0.009 part by mass or more, and is preferably 0.45 part by mass or less, more preferably 0.09 part by mass or less, and even more preferably 0.045 part by mass or less, with respect to 100 parts by mass of the water absorbent resin powder included in the absorbent article. If the amount of fumaric acid is 0.0009 part by mass or more, the deodorizing effect is further enhanced, and if the amount of fumaric acid is 0.45 part by mass or less, the amount of fumaric acid during use of the diaper can be lowered.

The member having fumaric acid disposed preferably includes a resin fiber. At least a part of the surface of the resin fiber is composed of a polyolefin resin, polyester resin, or polyamide resin. When such resin fibers are contacted with the fumaric acid-containing aqueous solution and dried to provide fumaric acid thereon, crystallization of fumaric acid progresses with time and fumaric acid is in a hardly dissolved state, thus the durability is further increased.

Examples of the polyolefin resin include polyethylene (PE), and polypropylene (PP). Examples of the polyester resin include polyethylene terephthalate (PET). Examples of the polyamide resin (PA) include polyamide 6, and polyamide 66.

The resin fiber may be a fiber composed of only one material, or a composite fiber composed of a plurality of materials. Examples of the composite fiber include a core-sheath type, side by side type, eccentric core-sheath type, radiational type, hollow radiational type, sea-island type, blend type, and block type. In the case that the resin fiber is the composite fiber, the resin fiber can further include a resin component other than the polyolefin resin, polyester resin and polyamide resin as the fiber material. Examples of the fiber composed of only one material include a polyolefin fiber, polyester fiber, and polyamide fiber. Examples of the composite fiber include a fiber having a core composed of a polyolefin resin and a sheath composed of a polyester resin, and a fiber having a core composed of a polyamide resin and a sheath composed of a polyester resin.

In the case that the resin fiber is a composite fiber having a surface formed from two or more resins, the area ratio of the region formed from the polyolefin resin, polyester resin or polyamide resin on the whole fiber surface is preferably 50% or more, more preferably 60% or more, and even more preferably 70% or more. If the area composed of the specific resin is 50% or more, the fumaric acid coating film has further enhanced durability. It is noted that the area ratio can be calculated based on the construction of the composite fiber.

The resin fiber is preferably the fiber composed of only one resin selected from the polyolefin resin, polyester resin and polyamide resin; or the core-sheath type composite fiber having the sheath composed of the polyolefin resin, polyester resin or polyamide resin.

Fumaric acid is preferably provided by contacting the above member (resin fiber) with a fumaric acid-containing aqueous solution, and then removing water. Fumaric acid forms a coating film on the resin fiber surface and crystalizes on the resin fiber surface by providing fumaric acid like this, thus fumaric acid hardly detaches from the resin fiber.

Examples of the method for contacting the resin fiber with the fumaric acid-containing aqueous solution include a method for immersing the resin fiber in the fumaric acid-containing aqueous solution, and a method for spraying or applying the fumaric acid-containing aqueous solution on the resin fiber. As the solvent of the fumaric acid-containing aqueous solution, water, a mixed solution of water and a hydrophilic organic solvent, or the like can be used. Examples of the hydrophilic organic solvent include methanol, ethanol, acetone, glycerin, ethylene glycol, and propylene glycol.

The concentration of fumaric acid in the fumaric acid-containing aqueous solution is preferably 0.03 mass % or more, more preferably 0.06 mass % or more, and even more preferably 0.10 mass % or more, and is preferably 0.60 mass % or less, more preferably 0.30 mass % or less. If the concentration of fumaric acid is 0.03 mass % or more, the concentration of fumaric acid is not excessively low, and adhesion of fumaric acid to the resin fiber and drying are easier, and if the concentration of fumaric acid is 0.60 mass % or less, it is easy to dissolve fumaric acid completely in the aqueous solution.

The fumaric acid-containing aqueous solution preferably contains a thickener. Examples of the thickener include xanthan gum, pectin, guar gum, tamarind gum, carrageenan, gelatin, unsaturated carboxylic acid polymer or copolymer (e.g. polyacrylic acid, isobutylene-maleic acid copolymer, diisobutylene-maleic acid copolymer, styrene-maleic acid copolymer, styrene-maleic acid-(meth)acrylate copolymer, (meth)acrylic acid-(meth)acrylate copolymer), polysaccharide carboxylate (e.g. carboxymethyl cellulose), salts thereof (e.g. organic amine salt, alkali metal salt, alkaline earth metal salt), naphthalene sulfonic acid formalin condensed product, polystyrene sulfonic acid, salts thereof (e.g. organic amine salt, alkali metal salt, alkaline earth metal salt), polyvinyl alcohol, polyethylene glycol, and inorganic acid (hydrochloric acid, phosphoric acid or the like) salt or organic acid (formic acid, acetic acid, lactic acid or the like) salt of N,N-dialkylaminoalkyl (meth)acrylate polymer or copolymer.

The amount of the thickener is not particularly limited, and is preferably 0,0000002 part by mass or more, more preferably 0,001 part by mass or more, and even more preferably 0.01 part by mass or more, and is preferably 5 parts by mass or less, more preferably 0.5 part by mass or less, and even more preferably 0.04 part by mass or less, with respect to 100 parts by mass of fumaric acid.

The fumaric acid-containing aqueous solution used for processing may further contain an organic acid such as citric acid and malic acid, an antibacterial agent, a deodorizer, a surfactant, an oil agent used for spinning, or the like, in addition to the thickener.

The method for removing water after contacting the sheet member with the fumaric acid-containing aqueous solution is not particularly limited, and examples thereof include a natural drying method.

The amount of fumaric acid to be added is preferably 0.00045 part by mass or more, more preferably 0.0009 part by mass or more, and is preferably 0.225 part by mass or less, more preferably 0.045 part by mass or less, and even more preferably 0.0225 part by mass or less, with respect to 100 parts by mass of the resin fiber. If the amount of fumaric acid to be added is 0.00045 part by mass or more, proliferation of putrefactive bacteria on the absorbent article after absorbing body fluid or the like can be further inhibited, and if the amount of fumaric acid to be added is 0.225 part by mass or less, the fumaric acid coating film is not excessively thick and thus has further enhanced durability. The amount of fumaric acid to be added is determined by Soxhlet extracting the fumaric acid-coating fiber having a determined mass using a large quantity of ethanol to completely dissolve the adhered fumaric acid, and then measuring the mass of fumaric acid in the solution.

It is noted that the timing to dispose fumaric acid is not particularly limited. For example, in case of supporting fumaric acid on the top sheet, fumaric acid is supported on the liquid permeable sheet in advance, and the fumaric acid-supporting sheet is used as the top sheet; or alternatively the liquid permeable sheet having no fumaric acid supported is used to assemble the absorbent article, and then the fumaric acid-containing aqueous solution is sprayed on the top sheet. In addition, in case of supporting fumaric acid on the pulp of the water absorbent layer, fumaric acid is supported on the pulp in advance, and the fumaric acid-supporting pulp is used to produce the water absorbent layer; or alternatively the pulp having no fumaric acid supported is used to produce the water absorbent layer, and then the fumaric acid-containing aqueous solution is sprayed on the water absorbent layer.

(Polyphenol Compound)

The absorbent article has a polyphenol compound disposed closer to the skin surface side than the back sheet. The position where the polyphenol compound is disposed is not particularly limited, as long as the polyphenol compound is closer to the skin surface side than the back sheet, and examples thereof include the top sheet, absorbent body, back sheet, sheet disposed between the top sheet and the absorbent body, and sheet disposed between the absorbent body and the back sheet. In the case that the polyphenol compound is disposed in the absorbent body, the polyphenol compound may be disposed in the water absorbent layer or on the liquid permeable sheet constituting the absorbent body. In addition, the polyphenol compound may be disposed in only one member or in two or more members.

The amount of the polyphenol compound is preferably 0.07 part by mass or more, more preferably 0.175 part by mass or more, and even more preferably 0.35 part by mass or more, and is preferably 3.5 parts by mass or less, more preferably 1.75 parts by mass or less, and even more preferably 0.7 part by mass or less, with respect to 100 parts by mass of the water absorbent resin powder included in the absorbent article. If the amount of the polyphenol compound is 0.07 part by mass or more, the deodorizing effect is further enhanced, and if the amount of the polyphenol compound is 3.5 parts by mass or less, the cost can be lowered.

In the absorbent article, the ratio of the total amount of the polyphenol compound to the total amount of fumaric acid (polyphenol compound/fumaric acid) is preferably 7.8 or more, more preferably 19.4 or more, and even more preferably 38.9 or more, and is preferably 388.9 or less, more preferably 194.4 or less, and even more preferably 77.8 or less. If the ratio is 7.8 or more, the initial deodorizing effect is further exerted, and if the ratio is 388.9 or less, the deodorizing effect is exerted for a long period of time.

Examples of the polyphenol compound include tannin, tannic acid, *Rhus chinensis*, gallnut, and gallic acid, and the polymer of the polyphenol compound is preferable, the condensed tannin is more preferable. The polyphenol compound can be used solely, or two or more of the polyphenol compounds can be used in combination.

The condensed tannin is included in fruit of persimmon (persimmon juice), immature banana, peel or seed of grape, chestnut skin, black tea, seed coat or pod of beans such as carob, tamarind and tara, bark or woody part of oak, quebracho or mimosa, and the like, and can be obtained as a concentrate by squeezing, or extracting with a solvent (e.g. heat water or alcohol).

The condensed tannin is preferably a compound having a plurality of hydroxy groups bonding to a flavan backbone, and more preferably a compound having hydroxy groups bonding to at least two carbon atoms selected from the group consisting of carbon atoms at 3-position, 5-position and 7-position and carbon atoms at 3'-position, 4'-position and 5'-position of phenyl group bonding to 2-position in a structural formula of a flavan backbone shown by the following formula (1). In particular, the condensed tannin is preferably a compound having a flavan backbone in which hydroxy groups bond to carbon atoms at least at 5-position, 7-position, 3'-position and 4-position, and it is known that many condensed tannins having such structure are present in natural materials. In addition, as the condensed tannin, a compound in which the hydroxy group bonding to the carbon atom at 3-position of the flavan backbone is esterified is also known, and a compound in which the hydrogen atom of the above-described hydroxy group is replaced with a galloyl group (3,4,5-trihydroxybenzoyl group) is known. It is considered that the condensed tannin interacts with the molecule causing the odor (odor molecule) at multiple points by its hydroxy groups bonding to the flavan backbone, and thus can fix the odor molecule.

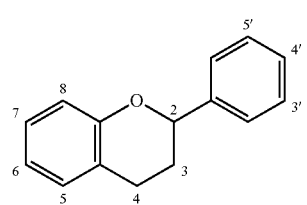

(1)

The condensed tannin is preferably a compound having a structure in which a plurality of flavan backbones having a plurality of hydroxy groups bonding thereto are bonded together via a carbon-carbon bond. It is considered that the condensed tannin having a plurality of flavan backbones bonded together can include the odor molecule therein and fix the same, and thus can enhance the deodorizing effect. For example, it is known that a condensed tannin having a plurality of flavan backbones bonded together in which the carbon atom at 4-position and the carbon atom at 8-position of the flavan backbone shown above are the bonding site is present in natural materials.

As the condensed tannin having a plurality of flavan backbones bonded together, for example, a compound having a repeating unit represented by the following formula (2) is preferably used. It is noted that $R^1$ represents a hydrogen atom or hydroxy group and $R^2$ represents a hydrogen atom or galloyl group in the following formula (2).

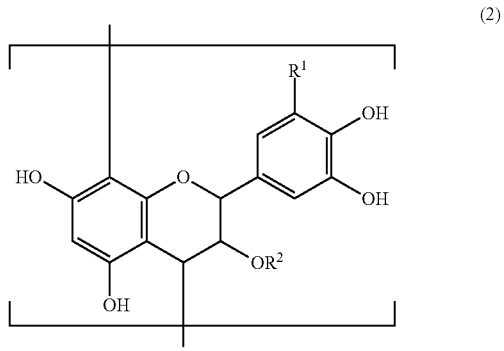

(2)

The weight average molecular weight of the condensed tannin is preferably 2,000 or more, more preferably 3,000 or more, and even more preferably 5,000 or more from the viewpoint of increasing the deodorizing effect. The condensed tannin having the above weight average molecular weight has a plurality of flavan backbones bonded together. On the other hand, the upper limit of the weight average molecular weight of the condensed tannin is not particularly limited, but the weight average molecular weight is preferably 500,000 or less, more preferably 300,000 or less, and even more preferably 150,000 or less from the viewpoint of increasing the solubility and hence improving the handling. The weight average molecular weight is a polystyrene converted value measured by gel permeation chromatography.

As the condensed tannin, the one from the persimmon juice (condensed tannin included in a squeezed juice of persimmon) is preferably used. The persimmon tannin that is the condensed tannin from the persimmon juice has a structure in which about 12 to 30 flavan backbones having a plurality of hydroxy groups bonding thereto are bonded together, and shows a very high deodorizing effect. The persimmon juice can be obtained, for example, by squeezing the fruit of immature astringent persimmon and fermenting the obtained squeezed juice. The persimmon juice may be used directly, or be suitably subjected to treatment such as concentration, dilution, filtration, extraction and drying, where necessary, As the persimmon juice, a commercially available product may be used.

A metal atom is preferably substituted for a part of the hydrogen atoms of the phenolic hydroxy groups in the condensed tannin. Substituting the metal atom for a part of the hydrogen atoms further enhances the performance capturing the molecule causing the odor (odor molecule). The metal atom is preferably an alkali metal atom, more preferably sodium or potassium.

The sheet member having the polyphenol compound disposed preferably includes a water absorbent fiber. The water absorbent fiber is not particularly limited, as long as the fiber has water absorption. It is noted that the water absorption is a phenomenon that a liquid water enters the fiber by a capillary action or the like.

Examples of the water absorbent fiber include a cellulose fiber, polyvinyl alcohol fiber, ethylene-vinyl alcohol fiber, and polyacrylic acid sodium salt fiber. Examples of the cellulose fiber include a natural cellulose fiber, and regenerated cellulose fiber. Examples of the natural cellulose fiber include cotton, linen, and wood pulp. Examples of the regenerated cellulose fiber include rayon, polynosic, cupra, and lyocell. Among them, the natural cellulose fiber and/or regenerated cellulose fiber is preferable, the natural cellulose fiber is more preferable. It is noted that the water absorbent fiber preferably does not includes an acetate fiber. It is also preferable that the sheet member having the polyphenol compound disposed consists of the natural cellulose fiber.

The amount of normal saline solution absorbed by per gram of the water absorbent fiber is preferably 0.2 g or more, more preferably 0.5 g or more, and even more preferably 1.0 g or more, and is preferably 5.0 g or less, more preferably 3.5 g or less, and even more preferably 2.0 g or less.

The member having the polyphenol compound disposed may further include a synthetic fiber other than the above water absorbent fiber. In this case, the amount of the water absorbent fiber in the fibers of the member is preferably 20 mass % or more, more preferably 30 mass % or more, and even more preferably 50 mass % or more. In addition, the member having the polyphenol compound disposed may consist of the water absorbent fiber.

The polyphenol compound is preferably provided by contacting the member (water absorbent fiber) with the polyphenol compound-containing aqueous solution and then removing water. When the water absorbent fiber is contacted with the polyphenol compound-containing aqueous solution, the water absorbent fiber absorbs water and simultaneously takes the dissolved polyphenol compound therein, and if water is removed, the polyphenol compound exists inside the water absorbent fiber. The polyphenol compound existing inside the water absorbent fiber is not washed away in the body fluid or the like, thus the deodorizing effect can be exerted for a long period of time.

Examples of the method for contacting the water absorbent fiber with the polyphenol compound-containing aqueous solution include a method for immersing the water absorbent fiber in the polyphenol compound-containing aqueous solution, and a method for spraying or applying the polyphenol compound-containing aqueous solution on the water absorbent fiber. As the solvent of the polyphenol compound-containing aqueous solution, water is used. The solvent may further contain an organic solvent (methanol, ethanol, acetone, glycerin, ethylene glycol, propylene glycol, or the like).

The concentration of the polyphenol compound in the polyphenol compound-containing aqueous solution is preferably 0.5 mass % or more, more preferably 1.0 mass % or more, and even more preferably 5.0 mass % or more, and is preferably 30.0 mass % or less, more preferably 20.0 mass % or less. If the concentration of the polyphenol compound is 0.5 mass % or more, the spraying amount of the polyphenol compound-containing aqueous solution in the manufacturing process can be lowered, and thus drying becomes easier, and if the concentration of the polyphenol compound is 30.0 mass % or less, the polyphenol compound is more easily dissolved.

The polyphenol compound-containing aqueous solution preferably contains a basic metal compound. The basic metal compound is a compound whose aqueous solution has pH of more than 7. The basic metal compound may be used solely, or two or more of them may be used in combination.

Examples of the basic metal compound include a carbonate such as sodium carbonate and potassium carbonate; and a hydroxide such as sodium hydroxide, calcium hydroxide, potassium hydroxide and magnesium hydroxide. Among them, in particular, the compound including an alkali metal component is more preferable. In addition, the basic metal compound preferably does not include an alkaline earth metal component in view of its adverse effect on the absorption performance of the water absorbent resin powder.

When the concentration of the polyphenol compound in the polyphenol compound-containing aqueous solution ranges from 0.5 mass % to 30.0 mass %, the amount of the basic compound is preferably adjusted such that the aqueous solution (25° C.) has pH in a range from 9.0 to 10.0.

It is noted that the timing to dispose the polyphenol compound is not particularly limited. For example, in case of supporting the polyphenol compound on the liquid permeable sheet constituting the absorbent body, the polyphenol compound is supported on the liquid permeable sheet in advance, and the polyphenol-supporting sheet is used to produce the absorbent body; or alternatively the liquid permeable sheet having no polyphenol compound supported is used to produce the absorbent body and then the polyphenol compound-containing aqueous solution is sprayed on the absorbent body.

(Absorbent Article)

The absorbent article has fumaric acid disposed at the position being able to be in contact with the body fluid absorbed in the absorbent article and the polyphenol compound disposed closer to the skin surface side than the back sheet. Fumaric acid and the polyphenol compound may be disposed at the same position or at different positions. Fumaric acid and the polyphenol compound are preferably disposed closer to the skin surface side than the water absorbent resin powder. In addition, fumaric acid is preferably disposed closer to the skin surface side than the polyphenol compound. By disposing like this, fumaric acid disposed on the skin surface side can retain the side of the absorbent article in contact with the user to weak acidity, even if in the case that the polyphenol compound is treated with the basic metal compound.

Examples of the structure of the absorbent article include (1) a structure comprising an absorbent body, a top sheet disposed on a skin surface side of the absorbent body, and a back sheet disposed on an external surface side of the absorbent body, wherein the polyphenol compound is disposed on a moisture permeable sheet constituting the absorbent body, and fumaric acid is disposed on the top sheet; (2) a structure comprising an absorbent body, a top sheet disposed on a skin surface side of the absorbent body, and a back sheet disposed on an external surface side of the absorbent body, wherein the polyphenol compound is disposed on a moisture permeable sheet constituting the absorbent body, and a sheet having fumaric acid supported is disposed between the absorbent body and the top sheet; (3) a structure comprising an absorbent body, a top sheet disposed on a skin surface side of the absorbent body, and a back sheet disposed on an external surface side of the absorbent body, wherein the polyphenol compound is disposed on a moisture permeable sheet constituting the absorbent body, and fumaric acid is disposed on the top sheet and the pulp in the water absorbent layer; and (4) a structure comprising an absorbent body, a top sheet disposed on a skin surface side of the absorbent body, and a back sheet disposed on an external surface side of the absorbent body, wherein the polyphenol compound is disposed on a moisture permeable sheet constituting the absorbent body, fumaric acid is disposed on the pulp in the water absorbent layer, and a sheet having fumaric acid supported is disposed between the absorbent body and the top sheet. It is noted that when the absorbent body has the water absorbent resin powder held between the first liquid permeable sheet and the second liquid permeable sheet, the polyphenol compound is preferably supported on the liquid permeable sheet disposed closer to the skin surface side than the water absorbent resin powder (water absorbent layer).

(Specific Example)

Examples of the absorbent article according to the present invention include absorbent articles for absorbing body fluid excreted from human body, such as a disposable diaper (tape type, pants type, pad type or the like), incontinence pad, and sanitary napkin. Examples of the absorbent article according to the present invention further include a disposable diaper used for pets, and sheet type absorbent article.

When the absorbent article is an incontinence pad, sanitary napkin or disposable auxiliary pad, for example, the absorbent body is disposed between the liquid permeable top sheet and the liquid impermeable back sheet. Examples of the shape of the incontinence pad, sanitary napkin or disposable auxiliary pad include an hourglass shape and a gourd shape. In addition, liquid impermeable side sheets may be formed on both sides in the width direction of the liquid permeable top sheet, where necessary. The side sheets are joined to the upper surface of the top sheet on both sides in the width direction, and the side sheets inward in the width direction from the joining points form one pair of rising flaps along both side edges of the absorbent body.

When the absorbent article is a disposable diaper, examples of the disposable diaper include a tape type disposable diaper having one pair of securing members on left and right sides of a back portion or front abdominal portion, and forming a pants type by the securing members when being worn; and a pants type disposable diaper having a waist opening and one pair of leg openings formed by joining a front abdominal portion and a back portion together.

When the absorbent article is a disposable diaper, in the disposable diaper, for example, a laminated body composed of an inner sheet and an outer sheet may form a diaper body composed of a front abdominal portion, a back portion and a crotch portion located therebetween, and the absorbent body and the diffusion sheet may be disposed on the crotch portion. In addition, the disposable diaper is composed of, for example, a laminated body having the absorbent body disposed between a top sheet and a back sheet, and the laminated body may include a front abdominal portion, a back portion and a crotch portion located therebetween. The inner sheet is preferably hydrophilic or water-repellent, and the outer sheet is preferably water-repellent.

Rising flaps are preferably provided along both side edge portions of the disposable diaper. Providing the rising flaps can prevent side leakage of the body fluid. The rising flaps may be formed by raising inward edges of side sheets provided on both sides in the width direction of the top sheet. The rising flaps and side sheet are preferably water-repellent.

Figure 2:
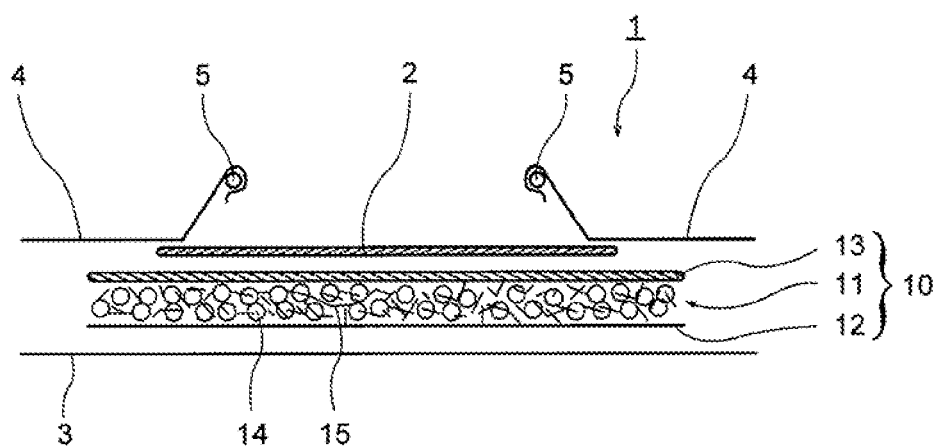
FIG. 2 is a schematic cross-sectional view along line V-V in FIG. 1.
Figure 3:
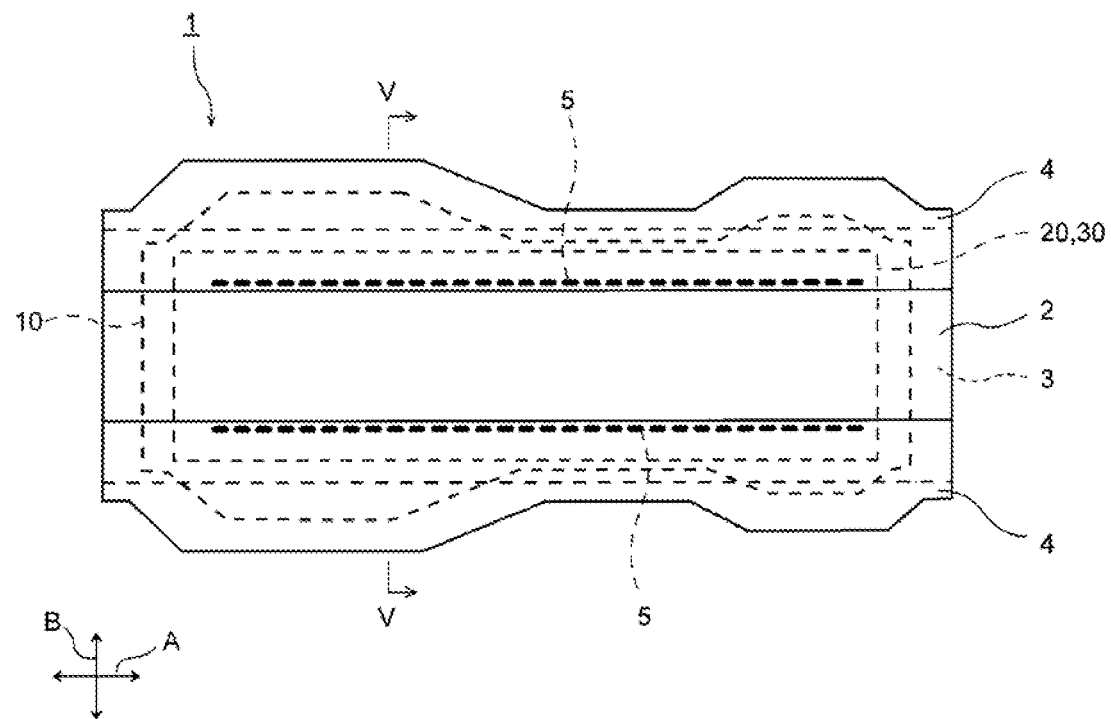
FIG. 3 is a planar view of another example of the absorbent article according to the present invention.
Figure 4:
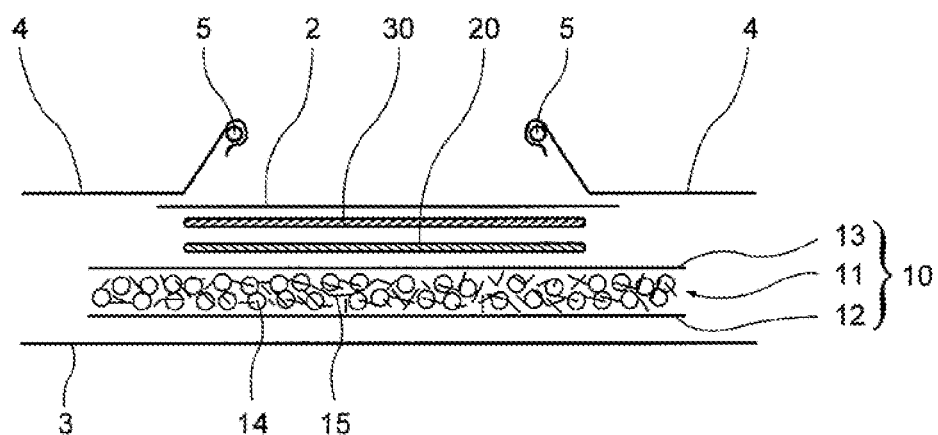
FIG. 4 is a schematic cross-sectional view along line V-V in FIG. 3.

Next, embodiments of the absorbent article will be described with reference to FIGS. 1 to 4 using an incontinence pad as an example. FIG. 1 shows a planar view of an incontinence pad according to the embodiment 1. FIG. 2 shows a V-V cross-sectional view of the incontinence pad in FIG. 1. FIG. 3 shows a planar view of an incontinence pad according to the embodiment 2, FIG. 4 shows a V-V cross-sectional view of the incontinence pad in FIG. 3. It is noted that, in the figures, the arrow B indicates a width direction, the arrow A indicates a longitudinal direction, and the direction on the surface formed by the arrows A and B is a planar direction.

Embodiment 1

The incontinence pad (absorbent article) 1 according to the embodiment 1 shown in FIGS. 1 and 2 comprises a liquid permeable top sheet 2, a liquid impermeable back sheet 3, and an absorbent body 10 disposed therebetween. The incontinence pad 1 according to the embodiment 1 has the absorbent body 10 as an absorbent body. The absorbent body 10 is composed of a first base material 12, a second base material 13, and a water absorbent layer 11 disposed therebetween. The water absorbent layer 11 is composed of a water absorbent resin powder 14 and a water absorbent fiber 15.

The top sheet 2 is a fumaric acid-supporting sheet having fumaric acid (not shown) supported. In addition, the second base material 13 constituting the absorbent body 10 is a polyphenol compound-supporting sheet having the polyphenol compound (not shown) supported. It is noted that, in FIG. 2, fumaric acid is supported only on the top sheet 2, but fumaric acid may also be supported on the water absorbent layer 11. In addition, in FIG. 2, the polyphenol compound is supported only on the second base material 13 constituting the absorbent body 10, but the polyphenol compound may be supported on the first base material 12 or on both of the first base material 12 and the second base material 13.

In FIGS. 1 and 2, the example using the absorbent body 10 with a gourd shape in the planar view as the absorbent body is shown, but the embodiment of the absorbent body is not limited to this. In FIGS. 1 and 2, the absorbent body 10 is composed of the first base material 12, the second base material 13 and the water absorbent layer 11 disposed therebetween, but the water absorbent layer 11 may be wrapped with the first base material 12, and the polyphenol compound may be supported on the first base material 12.

Side sheets 4 extending in the longitudinal direction A of the incontinence pad 1 are joined on both side edges in the width direction B of the top sheet 2. The side sheets 4 are formed of a liquid impermeable plastic film, a water-repellent nonwoven fabric, or the like. The side sheets 4 are provided with raising elastic members 6 at inward edges in the width direction of the incontinence pad 1. When the incontinence pad 1 is used, the inward edges of the side sheets 4 rise toward the wearer's skin through the contractive force of the raising elastic members 5 to prevent side leakage of excrement such as urine.

Embodiment 2

The incontinence pad (absorbent article) 1 according to the embodiment 2 shown in FIGS. 3 and 4 comprises a liquid permeable top sheet 2, a liquid impermeable back sheet 3, an absorbent body 10 disposed therebetween, a first sheet 20 disposed between the absorbent body 10 and the top sheet 2, and a second sheet 30 disposed between the first sheet 20 and the top sheet 2. In the incontinence pad 1, the rectangular first sheet 20 and the rectangular second sheet 30 are parallelly disposed in the longitudinal direction of the incontinence pad. It is noted that back sheet 3, side sheet 4 and raising elastic member 5 are same as those in the embodiment 1, thus the description regarding them is omitted.

The incontinence pad 1 according to the embodiment 1 has the absorbent body 10 as an absorbent body. The absorbent body 10 is composed of a first base material 12, a second base material 13, and a water absorbent layer 11 disposed therebetween. The first sheet 20 and the second sheet 30 have a planar view shape that is equal to or smaller than the planar view shape of the water absorbent layer 11. The water absorbent layer 11 is composed of a water absorbent resin powder 14 and a water absorbent fiber 15.

The polyphenol compound is supported on the first sheet 20. Fumaric acid is supported on the second sheet 30. In FIG. 4, the polyphenol compound is supported on the first sheet 20 and fumaric acid is supported on the second sheet 30, but fumaric acid may be supported on the first sheet 20 and the polyphenol compound may be supported on the second sheet 30. In addition, in FIG. 4, the first sheet 20 and the second sheet 30 are both disposed between the top sheet 2 and the absorbent body 10, but both of them may be disposed between the back sheet 3 and the absorbent body 10, or alternatively either one of them may be disposed between the back sheet 3 and the absorbent body 10, and another one may be disposed between the top sheet 2 and the absorbent body 10. It is noted that, in FIGS. 3 and 4, fumaric acid and the polyphenol compound are supported on different sheets, but both of fumaric acid and the polyphenol compound may be supported on the first sheet 20. In this case, the second sheet 30 is not necessary.

EXAMPLES

Next, the present invention will be described in detail by way of examples. However, the present invention is not limited to the examples described below. Various changes and modifications without departing from the spirit of the present invention are included in the scope of the present invention.

[Evaluation Methods]
(Evaluation of Deodorizing Effect (Open System))

The absorbent article was allowed to absorb 50 mL of a mixed human urine, and kept in a constant temperature reservoir of 40° C. for a predetermined time. After the predetermined time lapsed, the absorbent article was taken out from the constant temperature reservoir, and a sensory test was conducted to evaluate the odor from the top sheet side by a six-grade rating method ("Handbook Malodor Prevention Method Chapter IV", published by Gyosei Corporation). The sensory test was conducted by six persons, and the average value thereof was calculated.

Evaluation Standard
 0: no odor.
 1: a little odor.
 2: urine odor is scented out, but it is weak.
 3: urine odor is easily scented out.
 4: strong urine odor.
 5: very strong urine odor.

(Evaluation of Deodorizing Effect (Closed System))

The absorbent article was allowed to absorb 50 mL of a mixed human urine. The whole absorbent article was covered with a moisture permeable film (gas permeable film "PM-18" available from Tokuyama Corporation), and then kept in a constant temperature reservoir of 40° C. for a predetermined time. After the predetermined time lapsed, the absorbent article covered with the moisture permeable film was taken out from the constant temperature reservoir, and a sensory test was conducted to evaluate the odor leaking out of the moisture permeable film by a six-grade rating method ("Handbook Malodor Prevention Method Chapter IV" published by Gyosei Corporation). The sensory test was conducted by six persons, and the average value thereof was calculated, Evaluation Standard
 0: no odor.
 1: a little odor.
 2: urine odor is scented out, but it is weak.
 3: urine odor is easily scented out.
 4: strong urine odor.
 5: very strong urine odor.

(Polyphenol-Supporting Sheet)
Polyphenol-Supporting Sheet No. 1

The tannin-containing solution No. 1 was sprayed on a tissue paper (mass per unit area: 15.0 g/m$^2$, natural cellulose fiber: 100 mass %) and dried to produce the polyphenol-supporting sheet No. 1. The tannin-containing solution No. 1 contains a condensed tannin included in a squeezed juice of persimmon, and has pH in a range from 5.4 to 6.4. In addition, the amount of the condensed tannin supported on the polyphenol-supporting sheet No. 1 was adjusted to 0.7 g/m$^2$.

Polyphenol-Supporting Sheet No. 2

The tannin-containing solution No. 2 ("FG-22" available from Rilis Co. Ltd.) was sprayed on a tissue paper (mass per unit area: 15.0 g/m$^2$, natural cellulose fiber: 100 mass %) and dried to produce the polyphenol-supporting sheet No. 2. The tannin-containing solution No. 2 contains a condensed tannin included in a squeezed juice of persimmon and sodium carbonate, and has pH in a range from 9.0 to 10.0. The tannin-containing solution No. 2 contains 18.0 parts by mass to 180.0 parts by mass of sodium carbonate with respect to 100 parts by mass of the condensed tannin. In addition, the amount of the condensed tannin supported on the polyphenol-supporting sheet No. 2 was adjusted to 0.7 g/m$^2$. The polyphenol compound supported on the obtained polyphenol-supporting sheet has a part of the hydrogen atoms of the phenolic hydroxy groups replaced with a sodium atom.

Polyphenol-Supporting Sheet No. 3

The tannin-containing solution No. 1 was sprayed on a tissue paper (mass per unit area: 15.0 g/m$^2$, natural cellulose fiber: 100 mass %) and dried to produce the polyphenol-supporting sheet No. 3. The amount of the condensed tannin supported on the polyphenol-supporting sheet No. 3 was adjusted to 0.35 g/m$^2$.

(Fumaric Acid-Supporting Sheet)

A fumaric acid dispersion liquid having 30 mass % of fumaric acid dispersed in a xanthan gum aqueous solution (fumaric acid dispersion liquid "DF-30" available from Daiichi Seimo Co. Ltd, amount of xanthan gum with respect to 100 parts by mass of fumaric acid: 0.01 part by mass to 5 parts by mass) was dissolved in 100 parts by mass of water, to prepare the fumaric acid-containing aqueous solution No. 1 containing fumaric acid in a concentration of 0.15 mass %. A nonwoven fabric (thermal bond nonwoven fabric "LD18" available from Kinsei Seishi Co., Ltd., base fiber: core-sheath type composite fiber having polypropylene as core and polyethylene as sheath) was immersed in the fumaric acid-containing aqueous solution, and dried to provide the base fiber constituting the nonwoven fabric with fumaric acid. The amount of fumaric acid to be added with respect to 100 parts by mass of the nonwoven fabric was 0.0005 part by mass. It is noted that the amount of fumaric acid was calculated based on the mass difference before and after the immersion in the fumaric acid aqueous solution. The drying atmosphere was a temperature of 23° C.±5° C. and a humidity of 65%, and the drying time was 7 days.
(Polyphenol & Fumaric Acid-Containing Pulp)

The tannin-containing solution No. 1 was sprayed on the pulp and dried. It is noted that the spraying amount of the tannin-containing solution No. 1 was adjusted such that the amount of the condensed tannin was 0.175 part by mass with respect to 100 parts by mass of the pulp. Next, the fumaric acid-containing aqueous solution No. 1 was sprayed on the pulp and dried to prepare the polyphenol & fumaric acid-containing pulp. It is noted that the spraying amount of the fumaric acid-containing aqueous solution No. 1 was adjusted such that the amount of fumaric acid was 0.0045 part by mass with respect to 100 parts by mass of the pulp.

1. Effect Confirmation Test of Fumaric Acid

The absorbent article having neither polyphenol compound nor fumaric acid, the absorbent article only having the polyphenol compound, and the absorbent article having both the polyphenol compound and fumaric acid were produced, and the deodorizing performance of fumaric acid was evaluated.
(Production of Absorbent Article)
Absorbent Article No. 1

A synthetic rubber hotmelt adhesive was applied to a tissue paper, and then a mixture including pulp and a water absorbent resin powder ("Aqua Pearl®" DS560 available from San-Dia Polymers, Ltd.) was spread thereon (mass per unit area of water absorbent resin powder: 100 g/m$^2$) to form a water absorbent layer. A synthetic rubber hotmelt adhesive was applied to the water absorbent layer, and a tissue paper was laminated thereon to produce the absorbent body. The absorbent body had a width of 10 cm and a length of 10 cm.

A synthetic rubber hotmelt adhesive was applied to a liquid impermeable sheet (back sheet), and the absorbent body was laminated thereon. A synthetic rubber hotmelt adhesive was applied to the absorbent body, and a liquid permeable nonwoven fabric (top sheet) was laminated thereon to produce the absorbent article No. 1.
Absorbent Article No. 2

A synthetic rubber hotmelt adhesive was applied to a tissue paper, and then a mixture including pulp and a water absorbent resin powder ("Aqua Pearl®" DS560 available from San-Dia Polymers, Ltd.) was spread thereon (mass per unit area of water absorbent resin powder: 100 g/m$^2$) to form a water absorbent layer. A synthetic rubber hotmelt adhesive was applied to the water absorbent layer, and the polyphenol-supporting sheet No. 1 was laminated thereon to produce the absorbent body. The absorbent body had a width of 10 cm and a length of 10 cm.

A synthetic rubber hotmelt adhesive was applied to a liquid impermeable sheet (back sheet), and the absorbent body was laminated thereon. A synthetic rubber hotmelt adhesive was applied to the absorbent body, and a liquid permeable nonwoven fabric (top sheet) was laminated thereon to produce the absorbent article No. 2.
Absorbent Article No. 3

The absorbent article No. 3 was produced by the same method as that for producing the absorbent article No. 2 except that the liquid permeable nonwoven fabric of the top sheet was changed to the fumaric acid-supporting sheet.
Absorbent Article No. 4

A synthetic rubber hotmelt adhesive was applied to a tissue paper, and then a mixture including pulp and a water absorbent resin powder ("Aqua Pearl®" DS560 available from San-Dia Polymers, Ltd.) was spread thereon (mass per unit area of water absorbent resin powder: 100 g/m$^2$) to form a water absorbent layer. A synthetic rubber hotmelt adhesive was applied to the water absorbent layer, and the polyphenol-supporting sheet No. 2 was laminated thereon to produce the absorbent body. The absorbent body had a width of 10 cm and a length of 10 cm.

A synthetic rubber hotmelt adhesive was applied to a liquid impermeable sheet (back sheet), and the absorbent body was laminated thereon. A synthetic rubber hotmelt adhesive was applied to the absorbent body, and a liquid permeable nonwoven fabric (top sheet) was laminated thereon to produce the absorbent article No. 4.
Absorbent Article No. 5

The absorbent article No. 5 was produced by the same method as that for producing the absorbent article No. 4 except that the liquid permeable nonwoven fabric of the top sheet was changed to the fumaric acid-supporting sheet.

The deodorizing effects (open system) of the produced absorbent articles No. 1 to 5 were evaluated, and shown in Table 1.

TABLE 1

| Absorbent article No. | | 1 | 2 | 3 | 4 | 5 |
|---|---|---|---|---|---|---|
| Supported location | Fumaric acid | — | — | Top sheet | — | Top sheet |
| | Polyphenol compound | — | Upper layer of absorbent body | Upper layer of absorbent body | Upper layer of absorbent body | Upper layer of absorbent body |
| Amount of fumaric acid with respect to 100 parts by mass of water absorbent resin powder (parts by mass) | | — | — | 0.009 | — | 0.009 |
| Amount of polyphenol compound with respect to 100 parts by mass of water absorbent resin powder (parts by mass) | | — | 0.35 | 0.35 | 0.35 | 0.35 |
| Mass ratio (polyphenol compound/fumaric acid) | | — | — | 38.9 | — | 38.9 |
| Evaluation of deodorizing effect | Elapsed time (min) 0 | 2.75 | 2.25 | 2.00 | 2.00 | 2.00 |
| | 10 | 3.00 | 2.33 | 2.50 | 2.33 | 1.83 |
| | 60 | 3.29 | 2.71 | 2.71 | 2.57 | 2.00 |
| | 180 | 3.80 | 3.20 | 2.60 | 2.80 | 2.20 |
| | 360 | 4.20 | 3.60 | 2.60 | 3.20 | 2.20 | adhesive was applied to the absorbent body, and a liquid permeable nonwoven fabric (top sheet) was laminated thereon to produce the absorbent article No. 1.
Absorbent Article No. 2

A synthetic rubber hotmelt adhesive was applied to a tissue paper, and then a mixture including pulp and a water absorbent resin powder ("Aqua Pearl®" DS560 available from San-Dia Polymers, Ltd.) was spread thereon (mass per unit area of water absorbent resin powder: 100 g/m$^2$) to form The absorbent article No. 1 is the case having neither fumaric acid nor the polyphenol compound. The absorbent article No. 1 had the odor evaluated as 4.20 after 360 minutes. The absorbent articles No. 2 and 4 are the cases having the polyphenol compound disposed on the liquid permeable sheet (tissue paper) constituting the absorbent body. These absorbent articles No. 2 and 4 had the odor evaluated as 3.60, 3.20, respectively after 360 minutes, and thus had less odor than the absorbent article No. 1.

The absorbent articles No. 3 and 5 have fumaric acid disposed on the top sheet and the polyphenol compound disposed on the liquid permeable sheet (tissue paper) constituting the absorbent body. These absorbent articles No. 3 and 5 had the odor intensity of 2.60, 2.20, respectively after 360 minutes, and thus had less odor than the absorbent articles No. 2 and 4.

2. Effect Confirmation Test Based on Disposed Position of Polyphenol Compound and Fumaric Acid Absorbent articles having the polyphenol compound and/ or fumaric acid disposed at various positions were produced, and the deodorizing performance thereof based on the disposed position was evaluated.

(Production of Absorbent Article)
Absorbent Article No. 6

A synthetic rubber hotmelt adhesive was applied to a tissue paper, and then a mixture including pulp and a water absorbent resin powder ("Aqua Pearl®" DS560 available from San-Dia Polymers, Ltd.) was spread thereon (mass per unit area of water absorbent resin powder: 100 g/m$^2$) to form a water absorbent layer. A synthetic rubber hotmelt adhesive was applied to the water absorbent layer, and a tissue paper was laminated thereon to produce the absorbent body. The absorbent body had a width of 10 cm and a length of 10 cm.

A synthetic rubber hotmelt adhesive was applied to a liquid impermeable sheet (back sheet), and the absorbent body was laminated thereon. A synthetic rubber hotmelt adhesive was applied to the absorbent body, and a liquid permeable nonwoven fabric (top sheet) was laminated thereon to produce the absorbent article No. 6.

Absorbent Article No. 7

A synthetic rubber hotmelt adhesive was applied to a tissue paper, and then a mixture including pulp and a water absorbent resin powder ("Aqua Pearl®" DS560 available from San-Dia Polymers, Ltd.) was spread thereon (mass per unit area of water absorbent resin powder: 100 g/m$^2$) to form a water absorbent layer. A synthetic rubber hotmelt adhesive was applied to the water absorbent layer, and the polyphenol-supporting sheet No. 1 was laminated thereon to produce the absorbent body. The absorbent body had a width of 10 cm and a length of 10 cm.

A synthetic rubber hotmelt adhesive was applied to a liquid impermeable sheet (back sheet), and the absorbent body was laminated thereon. A synthetic rubber hotmelt adhesive was applied to the absorbent body, and the fumaric acid-supporting sheet was laminated thereon to produce the absorbent article No. 7.

Absorbent Article No. 8

A synthetic rubber hotmelt adhesive was applied to the polyphenol-supporting sheet No. 1, and then a mixture including pulp and a water absorbent resin powder ("Aqua Pearl®" D8560 available from San-Dia Polymers, Ltd.) was spread thereon (mass per unit area of water absorbent resin powder: 100 g/m$^2$) to form a water absorbent layer. A synthetic rubber hotmelt adhesive was applied to the water absorbent layer, and a tissue paper was laminated thereon to produce the absorbent body. The absorbent body had a width of 10 cm and a length of 10 cm.

A synthetic rubber hotmelt adhesive was applied to a liquid impermeable sheet (back sheet), and the absorbent body was laminated thereon. A synthetic rubber hotmelt adhesive was applied to the absorbent body, and the fumaric acid-supporting sheet was laminated thereon to produce the absorbent article No. 8.

Absorbent Article No. 9

A synthetic rubber hotmelt adhesive was applied to the polyphenol-supporting sheet No. 3, and then a mixture including pulp and a water absorbent resin powder ("Aqua Pearl®" DS560 available from San-Dia Polymers, Ltd.) was spread thereon (mass per unit area of water absorbent resin powder: 100 g/m$^2$) to form a water absorbent layer. A synthetic rubber hotmelt adhesive was applied to the water absorbent layer, and the polyphenol-supporting sheet No. 3 was laminated thereon to produce the absorbent body. The absorbent body had a width of 10 cm and a length of 10 cm.

A synthetic rubber hotmelt adhesive was applied to a liquid impermeable sheet (back sheet), and the absorbent body was laminated thereon. A synthetic rubber hotmelt adhesive was applied to the absorbent body, and the fumaric acid-supporting sheet was laminated thereon to produce the absorbent article No. 9.

Absorbent Article No. 10

A synthetic rubber hotmelt adhesive was applied to a tissue paper, and then a mixture including a polyphenol and fumaric acid-containing pulp and a water absorbent resin powder ("Aqua Pearl®" DS560 available from San-Dia Polymers, Ltd.) was spread thereon (mass per unit area of water absorbent resin powder: 100 g/m$^2$, mass per unit area of pulp: 200 g/m$^2$) to form a water absorbent layer. A synthetic rubber hotmelt adhesive was applied to the water absorbent layer, and a tissue paper was laminated thereon to produce the absorbent body. The absorbent body had a width of 10 cm and a length of 10 cm.

A synthetic rubber hotmelt adhesive was applied to a liquid impermeable sheet (back sheet), and the absorbent body was laminated thereon. A synthetic rubber hotmelt adhesive was applied to the absorbent body, and a liquid permeable nonwoven fabric (top sheet) was laminated thereon to produce the absorbent article No. 10.

The deodorizing effects (open system and closed system) of the produced absorbent articles No. 6 to 10 were evaluated, and shown in Table 2.

TABLE 2

| Absorbent article No. | | 6 | 7 | 8 | 9 | 10 |
|---|---|---|---|---|---|---|
| Supported Position | Fumaric acid | — | Top sheet | Top sheet | Top sheet | Pulp of water absorbent layer |
| | Polyphenol compound | — | Upper layer of absorbent body | Lower layer of absorbent body | Upper layer and lower layer of absorbent body | |
| Amount of fumaric acid with respect to 100 parts by mass of water absorbent resin powder (parts by mass) | | — | 0.009 | 0.009 | 0.009 | 0.009 |
| Amount of polyphenol compound with respect to 100 parts by mass of water absorbent resin powder (parts by mass) | | — | 0.35 | 0.35 | 0.35 | 0.35 |
| Mass ratio (polyphenol compound/fumaric acid) | | — | 38.9 | 38.9 | 38.9 | 38.9 |

TABLE 2-continued

| Absorbent article No. | | 6 | 7 | 8 | 9 | 10 |
|---|---|---|---|---|---|---|
| Evaluation of deodorizing effect (open system) | Elapsed time (min) | 0 | 3.00 | 2.41 | 2.00 | 2.19 | 2.49 |
| | | 10 | 3.59 | 1.87 | 2.47 | 2.47 | 2.84 |
| | | 60 | 3.69 | 2.21 | 2.62 | 2.51 | 2.92 |
| | | 180 | 4.12 | 2.21 | 2.80 | 2.44 | 3.12 |
| | | 360 | 4.63 | 2.78 | 3.20 | 2.89 | 3.33 |
| Evaluation of deodorizing effect (closed system) | Elapsed time (min) | 0 | 2.86 | 2.40 | 2.30 | 2.00 | 2.65 |
| | | 10 | 3.00 | 2.20 | 2.50 | 2.00 | 2.45 |
| | | 60 | 3.00 | 2.50 | 2.50 | 2.40 | 2.89 |
| | | 180 | 3.88 | 3.00 | 3.14 | 2.85 | 3.47 |
| | | 360 | 4.00 | 3.40 | 3.44 | 3.20 | 3.88 |

The absorbent article No. 6 is the case having neither fumaric acid nor the polyphenol compound. The absorbent article No. 6 had the odor evaluated as 4.00 after 360 minutes. The absorbent article No. 10 is the case having fumaric acid and the polyphenol compound disposed on the pulp of the water absorbent layer. The absorbent article No. 10 had the odor evaluated as 3.88 after 360 minutes, and thus had less odor than the absorbent article No. 6.

The absorbent articles No. 7 to 9 have fumaric acid disposed on the top sheet and the polyphenol compound disposed on the liquid permeable sheet (tissue paper) constituting the absorbent body. These absorbent articles No. 7 to 9 had the odor intensity of 3.40, 3.44, 3.20, respectively after 360 minutes, and thus had less odor than the absorbent article No. 10.

INDUSTRIAL APPLICABILITY

Examples of the absorbent article according to the present invention include absorbent articles used for absorbing body fluid excreted from human body, such as a disposable diaper (tape type, pants type, pad type or the like), incontinence pad, sanitary napkin, shoe insole, sweat-absorbing pad, adhesive bandage, and wound pad. Examples of the absorbent article according to the present invention further include a disposable diaper used for pets, and sheet type absorbent article.

REFERENCE SIGNS LIST

1: disposable diaper (absorbent article), 2: liquid permeable top sheet, 3: liquid impermeable back sheet, 4: side sheet, 5: elastic member, 10: absorbent body, 11: water absorbent layer, 12: first base material, 13: second base material, 14: water absorbent resin powder, 15: water absorbent fiber, 20: first sheet, 30: second sheet

The invention claimed is:

1. An absorbent article comprising a liquid permeable top sheet disposed on a skin surface side, a liquid impermeable back sheet disposed on an external surface side, and an absorbent body disposed between the top sheet and the back sheet, wherein
the absorbent body has a water absorbent layer including a water absorbent resin powder,
fumaric acid is disposed at a position being able to be in contact with body fluid absorbed in the absorbent article,
a polyphenol compound is disposed on a sheet member, the sheet member is disposed closer to the skin surface side than the back sheet, and
the sheet member consists of a natural cellulose fiber.

2. The absorbent article according to claim 1, wherein the polyphenol compound is a condensed tannin.

3. The absorbent article according to claim 1, wherein the polyphenol compound is a condensed tannin included in a squeezed juice of persimmon.

4. The absorbent article according to claim 1, wherein fumaric acid and the polyphenol compound are disposed closer to the skin surface side than the water absorbent resin powder.

5. The absorbent article according to claim 1, wherein a ratio of a total amount of the polyphenol compound to a total amount of fumaric acid (polyphenol compound/fumaric acid) ranges from 7.8 to 388.9.

6. The absorbent article according to claim 1, wherein an amount of the polyphenol compound ranges from 0.07 part by mass to 3.5 parts by mass with respect to 100 parts by mass of the water absorbent resin powder included in the absorbent article.

7. The absorbent article according to claim 1, wherein an amount of fumaric acid ranges from 0.0009 part by mass to 0.45 part by mass with respect to 100 parts by mass of the water absorbent resin powder included in the absorbent article.

8. The absorbent article according to claim 1, wherein the liquid permeable top sheet supports fumaric acid, and the absorbent body comprises a first liquid permeable sheet and a second liquid permeable sheet, and the water absorbent layer between the first liquid permeable sheet and the second liquid permeable sheet,
wherein the first liquid permeable sheet or the second liquid permeable sheet is the sheet member.

9. The absorbent article according to claim 8, wherein an amount of the polyphenol compound ranges from 0.07 part by mass to 3.5 parts by mass with respect to 100 parts by mass of the water absorbent resin powder included in the absorbent article, and an amount of fumaric acid ranges from 0.0009 part by mass to 0.45 part by mass with respect to 100 parts by mass of the water absorbent resin powder included in the absorbent article.

10. The absorbent article according to claim 1, wherein the liquid permeable top sheet supports fumaric acid, and the absorbent body comprises a first liquid permeable sheet and a second liquid permeable sheet, and the water absorbent layer between the first liquid permeable sheet and the second liquid permeable sheet,
wherein the first liquid permeable sheet and the second liquid permeable sheet are each the sheet member.

11. The absorbent article according to claim 10, wherein an amount of the polyphenol compound ranges from 0.07 part by mass to 3.5 parts by mass with respect to 100 parts by mass of the water absorbent resin powder included in the absorbent article, and an amount of fumaric acid ranges from 0.0009 part by mass to 0.45 part by mass with respect to 100 parts by mass of the water absorbent resin powder included in the absorbent article.

12. The absorbent article according to claim 1, wherein the liquid permeable top sheet supports fumaric acid, and the absorbent body comprises the water absorbent layer wrapped with a liquid permeable sheet, wherein the liquid permeable sheet is the sheet member.

13. The absorbent article according to claim 12, wherein an amount of the polyphenol compound ranges from 0.07 part by mass to 3.5 parts by mass with respect to 100 parts by mass of the water absorbent resin powder included in the absorbent article, and an amount of fumaric acid ranges from 0.0009 part by mass to 0.45 part by mass with respect to 100 parts by mass of the water absorbent resin powder included in the absorbent article.

14. The absorbent article according to claim 1, further comprises a first sheet between the liquid permeable top sheet and the absorbent body and a second sheet between the liquid permeable top sheet and the first sheet, wherein either one of the first sheet and the second sheet is the sheet member, and the other one of the first sheet and the second sheet supports the fumaric acid.

15. The absorbent article according to claim 14, wherein an amount of the polyphenol compound ranges from 0.07 part by mass to 3.5 parts by mass with respect to 100 parts by mass of the water absorbent resin powder included in the absorbent article, and an amount of fumaric acid ranges from 0.0009 part by mass to 0.45 part by mass with respect to 100 parts by mass of the water absorbent resin powder included in the absorbent article.

16. The absorbent article according to claim 1, wherein the polyphenol compound is disposed on a moisture permeable sheet constituting the absorbent body, fumaric acid is disposed on the liquid permeable top sheet, and the moisture permeable sheet is the sheet member.

17. The absorbent article according to claim 16, wherein the water absorbent layer further includes a pulp fiber and fumaric acid is further disposed on the pulp fiber in the water absorbent layer.

18. The absorbent article according to claim 1, wherein the polyphenol compound is disposed on a moisture permeable sheet constituting the absorbent body, a liquid permeable sheet supporting fumaric acid is disposed between the absorbent body and the liquid permeable top sheet, and the moisture permeable sheet is the sheet member.

19. The absorbent article according to claim 1, wherein the polyphenol compound is disposed on a moisture permeable sheet constituting the absorbent body, the water absorbent layer further includes a pulp fiber and fumaric acid is further disposed on the pulp fiber in the water absorbent layer, a liquid permeable sheet supporting fumaric acid is disposed between the absorbent body and the liquid permeable top sheet, and the moisture permeable sheet is the sheet member.

* * * * *